United States Patent
Coulon et al.

(10) Patent No.: US 9,400,252 B2
(45) Date of Patent: Jul. 26, 2016

(54) METHOD AND DEVICE FOR THE QUANTITATIVE LIBS MEASUREMENT OF BIO-MOLECULAR TARGETS ON A BIOCHIP

(71) Applicant: COMMISSARIAT A L'ENERGIE ATOMIQUE ET AUX ENERGIES ALTERNATIVES, Paris (FR)

(72) Inventors: Nadine Coulon, Dourdan (FR); Nicolas Ugolin, Paris (FR); Caroline Falck, Clamart (FR); Emilie Lefevre, Mennecy (FR); Sylvie Chevillard, Paris (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/428,101

(22) PCT Filed: Sep. 13, 2013

(86) PCT No.: PCT/EP2013/069072
§ 371 (c)(1),
(2) Date: Mar. 13, 2015

(87) PCT Pub. No.: WO2014/041145
PCT Pub. Date: Mar. 20, 2014

(65) Prior Publication Data
US 2015/0233837 A1    Aug. 20, 2015

(30) Foreign Application Priority Data
Sep. 13, 2012 (FR) .................. 12 58608

(51) Int. Cl.
*G01N 1/00* (2006.01)
*G01N 21/71* (2006.01)
*G01N 33/68* (2006.01)

(52) U.S. Cl.
CPC .......... *G01N 21/718* (2013.01); *G01N 33/6803* (2013.01); *G01N 2201/06113* (2013.01); *G01N 2333/4731* (2013.01); *G01N 2570/00* (2013.01)

(58) Field of Classification Search
CPC .......... G01N 2800/52; G01N 33/5008; G01N 21/718; G01N 2201/06113; G01N 2035/00326; G01N 2035/00495; G01N 35/026; G01N 35/00871; G01N 35/10; G01N 33/56983; G01N 21/25; G01N 2333/545
See application file for complete search history.

(56) References Cited

U.S. PATENT DOCUMENTS

| 5,656,504 A | 8/1997 | Johansson et al. |
| 2006/0014212 A1* | 1/2006 | Benkovic ............. B82Y 5/00 435/7.1 |

(Continued)

FOREIGN PATENT DOCUMENTS

| FR | 2929011 A1 | 9/2009 |
| FR | 2964458 A1 | 3/2012 |

(Continued)

*Primary Examiner* — Michael P Stafira
(74) *Attorney, Agent, or Firm* — Baker & Hostetler LLP (57) ABSTRACT

A process, for the quantitative analysis by optical emission spectroscopy of a plasma induced by a laser beam of at least one target included in a biochip, involves the use of an adjuvant allowing the formation of a dry matrix capable of being ablated simultaneously with the at least one target, the dry matrix being configured to improve the analytical properties of plasma, the adjuvant having an emission spectrum whose lines have wavelengths distinct from the wavelengths of the spectral lines used for the quantitative analysis of said at least one target.

14 Claims, 3 Drawing Sheets

(56) References Cited

U.S. PATENT DOCUMENTS

| | | |
|---|---|---|
| 2011/0000791 A1 | 1/2011 | Melin et al. |
| 2011/0109904 A1 | 5/2011 | Ugolin et al. |
| 2011/0171636 A1 | 7/2011 | Melikechi et al. |
| 2012/0099103 A1 | 4/2012 | Hahn |
| 2014/0085631 A1 | 3/2014 | Lacour et al. |
| 2015/0301058 A1* | 10/2015 | Schettini ............... G01N 33/53 424/193.1 |

FOREIGN PATENT DOCUMENTS

| | | |
|---|---|---|
| WO | 03025547 A1 | 3/2003 |
| WO | 2008156491 A2 | 12/2008 |

* cited by examiner

METHOD AND DEVICE FOR THE QUANTITATIVE LIBS MEASUREMENT OF BIO-MOLECULAR TARGETS ON A BIOCHIP

CROSS REFERENCE TO RELATED APPLICATIONS

This application is a National Stage of International patent application PCT/EP2013/069072, filed on Sep. 13, 2013, which claims priority to foreign French patent application No. FR 1258608, filed on Sep. 13, 2012, the disclosures of which are incorporated by reference in their entirety.

FIELD OF THE INVENTION

The present invention relates to a process and a device for the quantitative measurement of biomolecular targets on a biochip. It applies notably to the field of proteomics, and more particularly to the quantitative measurement of protein phosphorylation via a technique of optical emission spectroscopy on a laser-induced plasma.

BACKGROUND

In the field of proteomics, efforts are devoted toward identifying in cell extracts the proteins present and the respective concentrations thereof, and also toward identifying the post-translational modifications of these proteins, which are representative of their activity. One of the post-translational modifications that is of greatest interest in this context is phosphorylation: protein phosphorylation is fundamental from a cognitive viewpoint in the field of modern biology, or from a diagnostic viewpoint in the therapeutic field. This function is in fact essential in many biological processes, such as epigenetic regulation, nutritional regulation, DNA repair, hormone regulation, etc. No known simple and direct technique makes it possible to identify a protein in a biological medium and to evaluate its degree of phosphorylation.

One known analytical technique consists in analyzing protein extracts by taking them up on "spot" sites (each spot consisting of a plurality of identical probes) organized in an array on a support, commonly referred to as a biochip or microarray. The targets sought in the protein extracts to be analyzed are identified with specific probes that may be antibodies, receptors or any other molecule that specifically associates with a given protein or with one of its modifications. In the case of antibodies, the support is termed an "antibody biochip". A plurality of target biomolecules may thus be analyzed simultaneously or virtually simultaneously via suitable analytical techniques. Various techniques make it possible to perform the actual analysis of the elements thus retained or "segregated" on an antibody biochip.

For analysis of the phosphorylation of nucleic acids on a biochip, one known technique consists in performing this analysis via a technique of optical emission spectroscopy on a laser-induced plasma, commonly referred to by the abbreviation LIBS corresponding to the term laser-induced breakdown spectroscopy. This technique consists in ablating, by means of a laser beam, the segregated sample at the surface of the biochip and in generating a plasma, this plasma then being analyzed via a spectroscopic method. For each laser firing, the emission spectrum of the chemical elements investigated may be recorded, along with the focusing coordinates of the laser beam at the surface of the sample. Suitable calculation means may then make it possible to establish an elementary map of the surface of the sample. A device and a process for the quantitative measurement of biomolecular targets present on a biological analysis support are described, for example, in the patent application published under the reference FR 2 929 011. A LIBS analytical device is described, for example, in the patent application published under the reference FR 2 964 458.

However, a LIBS analysis of protein phosphorylation on a biochip poses several problems in principle. A first problem is associated with the presence of exogenous phosphorus, masking the signal sought. A second problem is associated with the fact that the supports usually used for biological analyses are incompatible with a LIBS analysis, since the plasmas which form on this type of support cannot be analyzed under acceptable conditions. A third problem is associated with the fact that biological molecules such as proteins have a very small amount of phosphorus in their structure, which is thus difficult to detect via LIBS. A fourth problem is associated with the fact that the signal obtained does not vary in a readily modelizable manner, for example linearly, as a function of the amount sought: in other words, normalization of the signal for the quantification of a protein is problematic.

One aim of the present invention is to overcome at least the abovementioned drawbacks, by proposing a process and a device for the quantitative analysis of biomolecular targets via a LIBS technique. This invention uses a suitable support and a process allowing the formation of a plasma that is readily analyzable by spectrometry, the LIBS signal emitted by the plasma being proportional to the abundance of the amount sought.

To this end, one subject of the invention is a process and a device for quantitative measurement. More specifically, one subject of the present invention is a process for the quantitative analysis by optical emission spectroscopy of a plasma induced by a laser beam of at least one target included in a biochip, characterized in that it involves the use of an adjuvant allowing the formation of a dry matrix capable of being ablated simultaneously with said at least one target, the dry matrix being configured to improve the analytical properties of plasma, the adjuvant having an emission spectrum whose lines have wavelengths distinct from the wavelengths of the spectral lines used for the quantitative analysis of said at least one target.

In one embodiment of the invention, said at least one target may be segregated on the biochip via at least one probe so that a probe-target complex is formed between each probe and the target corresponding thereto.

In one embodiment of the invention, said use of an adjuvant may allow the formation of a dry matrix of amorphous structure.

In one embodiment of the invention, said use of an adjuvant may allow the formation of a dry matrix of crystalline structure.

In one embodiment of the invention, the dry matrix may be formed such that the probe-target complexes are available at the surface of a support, and are totally or partially englobed by a volume of said dry matrix.

In one embodiment of the invention, the dry matrix and the probes may be fixed to a support.

In one embodiment of the invention, the adjuvant molecules forming the dry matrix may be directly complexed to the probes.

In one embodiment of the invention, the adjuvant molecules forming the dry matrix may be fixed to a support, the probes being fixed to the adjuvant molecules, the adjuvant molecules being fixed to the support.

In one embodiment of the invention, a layer of dry matrix may be formed by placing a layer of adjuvant on the surface of the support, prior to placing the probes on the surface of dry matrix thus formed at the surface of a support.

In one embodiment of the invention, the dry matrix may be formed by a compound whose absorption wavelengths are close to the wavelength of the laser beam, such that the wavelength used for the laser is included in the absorption spectrum of the dry matrix.

In one embodiment of the invention, the adjuvant may comprise a solution of water and of an element from the group comprising sugar, polysaccharide and disaccharide.

In one embodiment of the invention, each probe may be marked with a normalization element forming an internal standard.

In one embodiment of the invention, each probe may be marked with the normalization element by grafting.

In one embodiment of the invention, the normalization element may be formed by boron.

A subject of the present invention is also a device comprising a support comprising a plurality of sites, each site comprising a plurality of probes, the probes being grafted concomitantly to the molecules of an adjuvant allowing the formation of a dry matrix.

In one embodiment of the invention, said support may comprise organic compounds, monolithic compounds or organo-diamond compounds.

A subject of the present invention is also a solution for performing a process according to any one of the described embodiments, characterized in that it comprises an adjuvant allowing the formation of a dry matrix.

In one embodiment of the invention, the solution for performing a process according to one of the described embodiments may comprise a given proportion of an element for normalizing an optical signal of a plasma induced by a laser beam.

Another advantage afforded by the present invention is that it allows simple, rapid, quantitative and vectorial analysis of biomolecules, for example proteins, and of the phosphorus content in a mixture.

According to the present invention, a quantitative analysis is performed on a biochip comprising an array of targets and/or probes organized in spots. The spots of each probe are capable of recognizing and segregating a target biomolecule present in the mixture to be analyzed. According to one specificity of the present invention, it is proposed that an adjuvant be used to allow the formation of a dry matrix, this matrix being intimately linked with the targets or with the probe-target complexes. The term "intimately linked" means here that the dry matrix supports, englobes or surrounds the targets or the probe-target complexes, in a manner such that the laser ablation of the target or of the probe-target complex and the plasma produced by LIBS at a spot of the biochip array comprises, in addition to the target biomolecules or the target-probe complexes, adjuvant molecules and/or decomposition elements thereof. Hereinbelow, it is considered that a dry matrix is in the form of a solid compound of crystalline or amorphous form after drying of the biochip. As a nonlimiting example, the dry matrix may be in the form of an adduct, i.e. a mixture of probes, targets and adjuvant molecules, of a mixed crystalline or amorphous phase or englobing the targets and/or the probes. Various configurations of the dry matrix on the biochip support are described below as examples, with reference to FIGS. 2A to 2D. It should be observed that a process or a device according to the present invention may also apply to a biochip comprising a plurality of targets deposited or segregated on a support, not necessarily associated with probes.

The adjuvant is notably chosen so as to be essentially non-phosphorized, and so that it does not denature the antigen-antibody bond. This means, firstly, that the emission spectra of the molecules constituting the adjuvant and the matrix itself are different from the emission lines used to quantify the phosphorus and, where appropriate, to normalize the signal, and secondly that the adjuvant is compatible with the hybridization or complexation of the targets and/or of the probe-target complexes.

The adjuvant used for the formation of the dry matrix may, for example, be soluble. Examples of suitable solutions are described below. The dry matrix is also chosen so as moreover to have the advantage of improving the analytical properties of the plasma produced by the laser for the analysis via a spectroscopy technique. Notably, the dry matrix may be formed by a compound whose absorption wavelengths are close to the wavelength of the laser beam used, such that the wavelength used for the laser is included in the absorption spectrum of the dry matrix.

SUMMARY OF THE INVENTION

BRIEF DESCRIPTION OF THE DRAWINGS

Other characteristics and advantages of the invention will become apparent on reading the description, which is given as an example, with regard to the attached drawings, which represent.

DETAILED DESCRIPTION

Figure 1:
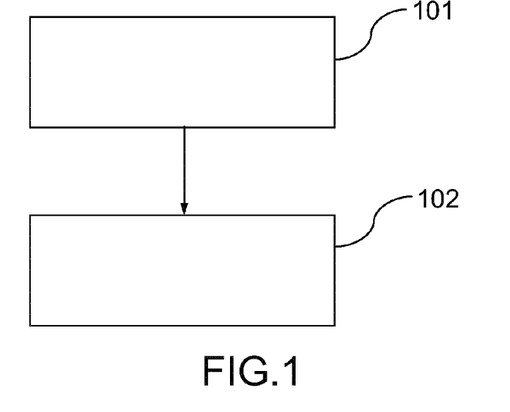
FIG. 1, a flow chart illustrating an analytical process according to one implementation example of the present invention.

With reference to FIG. 1, an analytical process according to any nonlimiting example of the present invention may comprise a first step 101 of preparing the biochip. First step 101 may be followed by a second step 102 of analysis via LIBS, during which a plasma is notably formed substantially on the target biomolecules to be analyzed, by means of an ablation laser, according to techniques that are known per se.

Preparation step 101 may comprise a first sub-step that consists in depositing biomolecules, i.e. targets alone and/or probes on a support, followed by drying; a second sub-step may consist, after an optional saturation sub-step, in segregating on the support a plurality of target biomolecules optionally by coupling them to antibodies corresponding thereto, forming a probe matrix. Each target biomolecule is thus fixed to a probe which recognizes it located on the support.

During the first step 101, the formation of a dry matrix is also performed, according to a specificity of the present invention. The dry matrix formed makes it possible to ensure better exploitability by optical emission spectroscopy of the plasma produced by the laser during the second step 102. The dry matrix is formed so as to be able to be ablated simultaneously with a target or with a probe-target complex. Thus, firing of the ablation laser targeting the target biomolecule of interest ensures the ablation of part of the neighboring dry matrix. To this end, the dry matrix may be arranged so as to completely or partially englobe the target biomolecule or the probe-target complex. The dry matrix may also be arranged below the target biomolecule or the probe-target complex, provided that the proximity of the dry matrix is sufficient for a laser firing intended for the target biomolecule or the probe-target complex also to ablate part of the neighboring dry matrix. Various possible configurations of the dry matrix relative to a given target biomolecule or given probe-target complex, on a biochip support, are described below with reference to FIGS. 3A to 3D.

The dry matrix is also configured so as to allow an improvement in the analytical properties of the LIBS plasma. In addition, this matrix should not denature the probe-target recognition, where appropriate, and should not itself contain phosphorus.

The dry matrix may be amorphous or crystalline, and may be formed by means of an adjuvant. The adjuvant may be, for example, a soluble adjuvant.

In practice, in one particular embodiment, a solution for an analytical process according to one of the described embodiments, comprising a proportion of biomolecules to be analyzed, may also comprise the adjuvant allowing the formation of the dry matrix. In certain embodiments, the adjuvant may be introduced into at least one of the solutions used for hybridizing the biochip with the target proteins or for rinsing the biochip after hybridization. In this embodiment, after complexation and/or rinsing, the adjuvant allows the formation of a dry matrix at the surface of the biochip notably at the various spots.

In other embodiments, the adjuvant forming a dry matrix may be introduced during the step of deposition of the probes onto the support at the time of manufacture of the biochip: either by introduction into the probe deposition solution, or just after the deposition of the probes, by chemically grafting the adjuvant molecule directly onto the surface of the support used for fixing the probes. For example, sucrose molecules may be grafted onto the surface of the biochip, activated with $SOCl_2$ by means of their alcohol function.

In another embodiment, the adjuvant molecules may first be grafted onto the surface of the biochip support and then activated, if need be, as a function of the nature of the adjuvant, and the probes may be grafted as spots onto the surface of the biochip by means of the adjuvant molecules.

Advantageously, at least one rinsing or hybridization solution may comprise a metallic or halogenated normalization element, emitting a LIBS signal different from that of phosphorus and proportional to the abundance of said metallic element. Said normalization element may be chosen notably such that it is in the same spectral window as the emission line chosen for the phosphorus analysis as a function of the apparatus used. Preferably, the emission lines may be different in the sense of the spectrograph used, i.e. sufficiently remote for a given spectrograph, in order for them to be able to be distinguished.

In general, the normalization element may be introduced into the adjuvant allowing the formation of the dry matrix.

The normalization element may be, for example, boron, taken in isolation, integrated into a molecule or trapped in a molecular cage or a crypt, and reproducibly bonded to the target.

Advantageously, the normalization element such as boron may be directly complexed to the probe antibody, or optionally to the target.

Examples of configurations of the normalization element relative to target molecules and/or probes are described below with reference to FIGS. 4A and 4B.

The support forming the biochip may be a phosphorus-free carbon-based support, comprising organic compounds, i.e. any combination of the elements carbon, hydrogen, oxygen and nitrogen. The support forming the biochip may be monolithic (such as diamond), vitreous, or organo-diamond, promoting the formation of a plasma that is exploitable under good conditions. It may be a support consisting of monolithic nanoparticles covered with probes deposited or grafted onto a vitreous or organic support.

The adjuvant introduced above, allowing the formation of the dry matrix, is itself configured so as not to denature the probe-target bond, and not to contain phosphorus. The adjuvant may be formed, for example, by polysaccharides, such as sucrose or any other polysaccharide not containing phosphorus.

The abovementioned second step 102 allows an analysis by spectrometry of LIBS type, using suitable devices, and may comprise process sub-steps that are themselves known. The second step 102 involves the use of analytical means via LIBS spectrometry, notably comprising at least means for emitting an intense pulsed laser beam or "ablation beam", means for moving the sample to be analyzed, recording detection means and calculation means.

Figure 2:
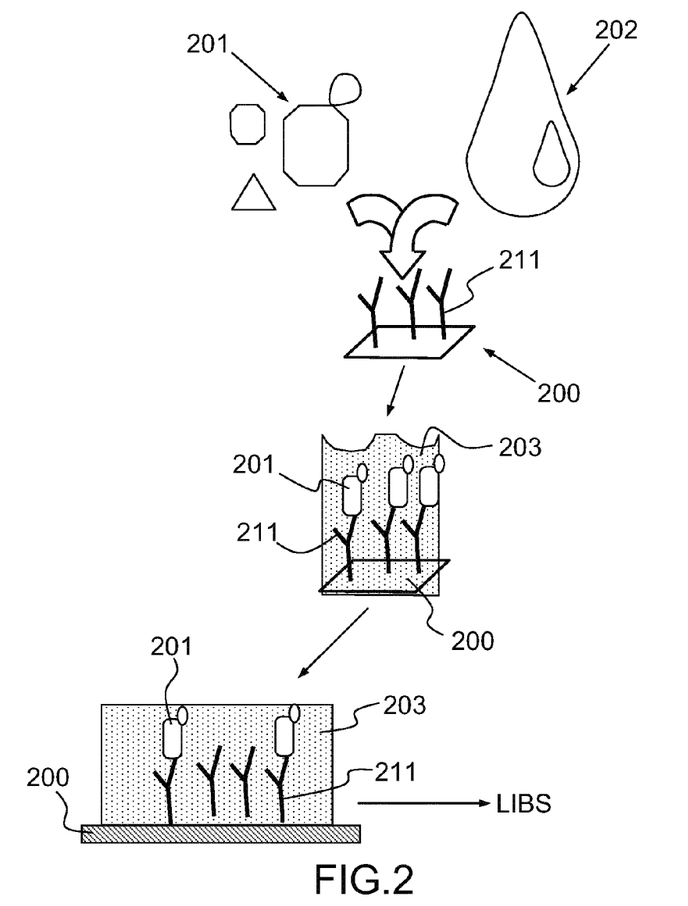
FIG. 2, a scheme illustrating the general principle of an analytical process on a biochip comprising probes/targets according to one implementation example of the present invention.

FIG. 2 is a scheme illustrating the general principle of an analytical process according to one implementation example of the present invention.

According to the general principle of the present invention when it applies to target proteins, a plurality of target proteins 201 may be deposited as a plurality of spots onto a support 200 of a biochip. In the example illustrated in FIG. 2, the support 200 also comprises a plurality of probes 211 that are capable of recognizing the target proteins 201. An analytical process according to the present invention involves the use of an adjuvant 202, for example a soluble adjuvant, allowing the formation of a dry matrix 203, totally englobing the probe-target complexes in the example illustrated in FIG. 2. Thus, after the abovementioned first step 101, described previously with reference to FIG. 1, the biochip comprising a plurality of target proteins 201 and also a plurality of probes 211 in the nonlimiting illustrated example of the present invention, may be subjected to a LIBS analysis during the abovementioned second step 102 and described with reference to FIG. 1.

FIGS. 3A to 3D are schemes synoptically illustrating an analytical device according to various implementation examples of the present invention, corresponding to various configurations of the dry matrix and of the biochip support.

Figure 3A:
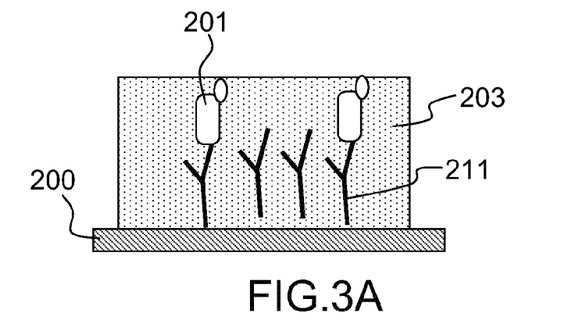
FIGS. 3A, 3B, 3C and 3D, schemes synoptically illustrating an analytical device in various configurations, according to implementation examples of the present invention.

In one embodiment illustrated by FIG. 3A, corresponding to a first configuration of the target biomolecules, corresponding probes and dry matrix on the biochip support, each target biomolecule 201 fixed to a probe 211 recognizing it arranged on the support 200 of the biochip may be englobed by a volume of dry matrix 203 formed by a suitable adjuvant as described previously. The probe-target biomolecule couple 211, 201 may be completely englobed by the dry matrix, as in the example illustrated by the figure, or only partially englobed thereby.

Figure 3B:
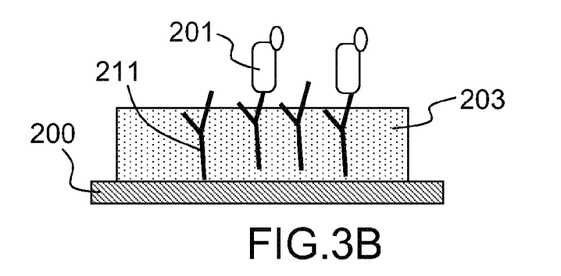

According to one embodiment illustrated by FIG. 3B, corresponding to a second configuration, the support 200 of the biochip, on which are placed the probes for forming the probe-target biomolecule couples 211, 201, may be saturated at its surface with the dry matrix 203. According to the second configuration, an adjuvant layer may be placed, for example, on the surface of the support 200 of the biochip already populated with probe-target biomolecule couples 211, 201.

Such an embodiment may have an advantage in terms of ease of use, the entire surface of the support 200 of the biochip possibly being saturated with the dry matrix 203.

Figure 3C:
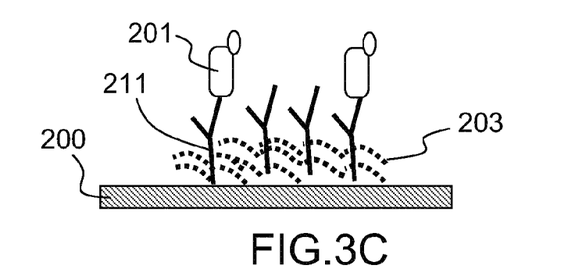

According to an embodiment illustrated by FIG. 3C, corresponding to a third configuration, each probe-target biomolecule couple 211, 201 placed on the support 200 of the biochip may be englobed in the dry matrix 203, the adjuvant forming the dry matrix 203 possibly being directly complexed to the probe 211.

Figure 3D:
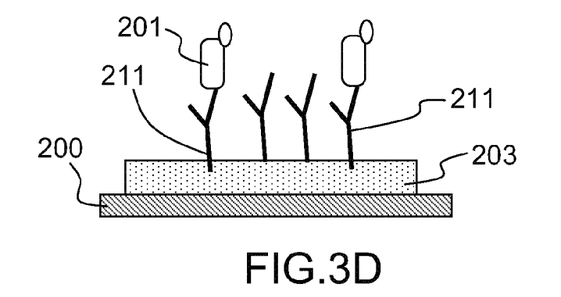

According to one embodiment illustrated by FIG. 3D, corresponding to a fourth configuration, a layer of the dry matrix 203 may be formed by placing or grafting a layer of adjuvant, for example, uniformly on the surface of the support 200 of the biochip, prior to placing the probes 211 grafted directly onto the matrix. The target biomolecule complexes or hybridizes to the probe corresponding thereto directly on the dry matrix. An alternative mode may consist in grafting the probes onto the support and then grafting onto the support the molecules of the matrix so as to surround the targets therewith. The fourth embodiment has a substantial advantage from an industrial viewpoint. Specifically, kits comprising a biochip on the support from which was formed the layer of dry matrix 203 may be supplied, like conventional biochips. An operator can then normally place the probe-target biomolecule couples on the surface of such a biochip by proceeding in a usual manner.

A subject of the present invention is also a device or "kit" for prehybridization or hybridization of biochips such as at least one solution for the prehybridization, hybridization or rinsing of a biochip comprising an adjuvant allowing the formation of a dry matrix at the surface of the biochip.

Thus, a subject of the present invention is also a biochip whose support thus comprises at its surface a layer of dry matrix 203.

Irrespective of the embodiment considered, it may be advantageous for the thickness of the dry matrix 203 formed over the target biomolecules not to be on average greater than 1 millimeter. For greater thicknesses, the plasma formed by the laser might in fact not contain traces of the target biomolecule in reasonable proportions for an analysis to be possible.

In each of the described embodiments, each probe 211 may advantageously comprise a normalization element forming an internal standard making it possible to normalize the signal obtained by LIBS. According to one specificity of the present invention, as has been described previously, the normalization element may be formed by an element that is directly complexed to each probe 211, for example via a grafting technique. If the probe 211 is formed by an antibody, the antibody may thus be directly labeled with the normalization element by grafting. The normalization element may, for example, be formed by an element such as boron.

Examples of configurations of the normalization element relative to target molecules and/or probes are described below with reference to FIGS. 4A and 4B, corresponding, respectively, to configurations 3A and 3C described previously.

Figure 4A:
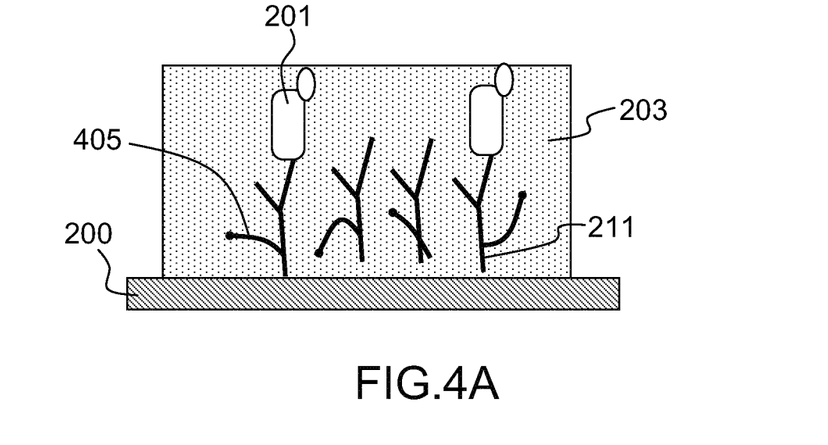
FIGS. 4A and 4B, schemes synoptically illustrating an analytical device also comprising a normalization element, in configurations corresponding, respectively, to FIGS. 3A and 3C.

With reference to FIG. 4A, a normalization element 405 may be fixed directly to a probe 211 placed on the support 200, for example via a grafting technique. The assembly formed by the probes 211 and the targets 201 may be englobed by the dry matrix 203 according to a configuration corresponding to the first configuration described previously with reference to FIG. 3A.

Figure 4B:
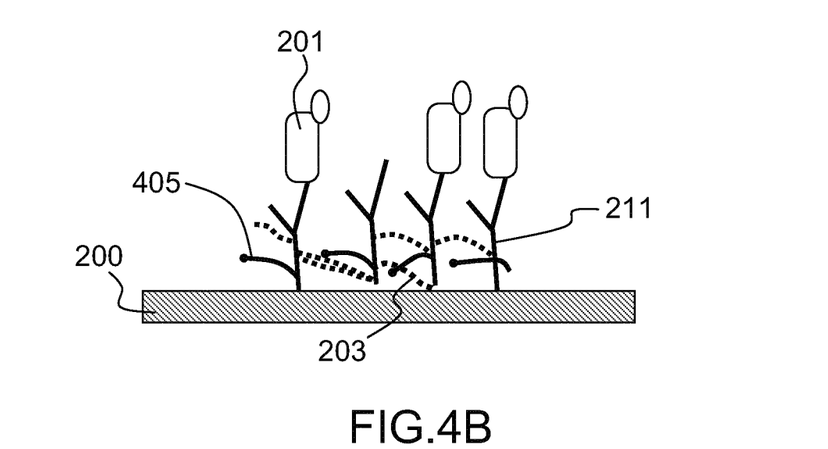

With reference to FIG. 4B, a normalization element 405 may be fixed directly to a probe 211 placed on the support 200, for example via a grafting technique. The adjuvant molecules forming the dry matrix 203 may, in such an example, be directly complexed to the probes 211, according to a configuration corresponding to the third configuration described previously with reference to FIG. 3C.

The spectral lines of the adjuvant have wavelengths different from the wavelengths of the spectral lines used for the quantitative analysis, comprising the spectral lines used for the normalization and the spectral lines used for the quantification of the target and/or of its post-translational modifications.

It is proposed hereinbelow to describe in detail two qualifications of a process according to one of the embodiments of the present invention, performed by the Applicant. The Applicant made qualifications of the analytical process by notably performing an analysis of phosphorylated protein, more specifically on an in vitro model reconstituted from an A2 beta-casein protein in which solutions of known concentrations of casein qualified by an analytical method of inductively coupled emission spectrometry type, commonly referred to by the abbreviation ICP-AES corresponding to inductively-coupled plasma—atomic emission spectrometry, are analyzed; and moreover in a biological model containing exogenous phosphorus for which the degree of phosphorylation of a molecular target H2AX may be induced at will. The process and devices associated with this analysis are presented in detail hereinbelow, according to a nonlimiting implementation example of the present invention, of the processes and devices that may be applied to the analysis of other target biomolecules, and notably of any phosphorylated protein. It should be observed that the example described below does not in any way limit the present invention, and corresponds to a particular case in which the adjuvant is introduced during each process step, and in which the dry matrix is formed therein on the biochip support so as to englobe the target biomolecule according to the embodiment described previously with reference to FIG. 2A. However, the various alternative modes described above with reference to FIGS. 2B to 2D might also, without preference, be applied and lead to similar results. Also, it is possible for the adjuvant to be introduced only during a single process step.

Example of Deposition of Targets on Biochip (Probe-Free Protein Chip)

The molecular mass of A2 beta-casein is equal to 23.983 kilodaltons. This protein may be supplied, for example, in lyophilized form and then purified, for example, via a method commonly referred to by the abbreviation HPLC corresponding to high-performance liquid chromatography, for example using a solution comprising water ($H_2O$), trifluoroacetic acid (TFA) and methyl cyanide (or acetonitrile). The protein concentration may be determined, for example, by means of UV spectrophotometry.

In order to evaluate the efficacy of the analysis by LIBS spectrometry, an analysis of the phosphorylation of beta-casein may be performed via a known and reputably reliable alternative method in order to provide reference measurements. To this end, it is possible to make use of an analytical method of ICP-AES type, this method being a reference method for determining the elemental composition of liquid compounds. The Applicant performed the ICP-AES analysis of beta-casein solutions with concentrations of 0, 4, 12 and 20 μM (micromoles).

In order to determine the sensitivity of LIBS spectrometry for the quantification of protein phosphorylation, various amounts of beta-casein are directly deposited on the support made of Kapton-epoxy, the Kapton-epoxy film being bonded, for example, using a cyanoacrylate adhesive onto a microscopy glass (for example in the form of a 7.5×2.5 cm slide).

The beta-casein solution thus obtained is serially diluted to concentrations of 0, 40, 85, 170, 257 and 350 μM in a buffered 0.1 M tris solution at pH 7.5, this preparation being referred to as "preparation A", in a buffered solution comprising 0.1 M of tris at pH 7.5 and 1 mM of sucrose, referred to as "preparation B", and in a buffered solution comprising 0.1 M of tris at pH 7.5, 1 mM of sucrose and 0.5 mM of boron, referred to as "preparation C". Each of these preparations was individually deposited in five replications on the Kapton-epoxy film, and dried for 30 minutes at room temperature.

Example of an Antibody Biochip

Lymphocytes may be isolated by gradient cell separation, starting with heparinized human blood samples. The cells are washed twice with phosphate-buffered saline or PBS, diluted to a concentration of $10^6$ cells/ml in a culture medium, for example a medium comprising 10% fetal calf serum or FCS, 1% of penicillin-streptomycin, and immediately irradiated with a cobalt-60 irradiator at a dosage level of 2 Gray·min$^{-1}$ at 0, 0.5, 2 and 4 Gray. After irradiation, the cells are rapidly diluted in a culture medium at a concentration of $5\times10^5$ cells/ml and incubated for one hour at a temperature of 37° C. in an atmosphere comprising a concentration of 5% carbon dioxide, before quantification of the phosphorylation level of γH2AX.

In order to obtain a matrix suitable for quantification of the phosphorylation via a LIBS analysis, it is necessary for the antibody matrix itself to be free of phosphorus. The anti-γH2AX$^{ser139}$ antibody may be chosen for this purpose. The dialyzed antibody is then deposited on a support formed from Kapton or Kapton-epoxy, for example a support comprising a 25 μm layer of Kapton, or a 25 μm layer of Kapton covered with a 25 μm layer of epoxy.

The antibody is placed on the film layer of Kapton-epoxy. A volume of 100 μl of anti-γH2AX$^{ser139}$ is dialyzed in a buffered solution of pH 7.5 comprising 0.1 M of tris and 1 mM of sucrose, for four hours at a temperature of 4° C.

After dialysis, the concentration of the anti-γH2AX$^{ser139}$ solution is adjusted to 0.5 mg/ml in 1 mM of boron in a buffered 0.1 M tris solution, and a volume of 1 μl of the solution is placed in each well of the matrix on the film layer of Kapton-epoxy, and is then dried for 30 minutes at room temperature. In order to avoid non-specific bonding of proteins to the film layer of Kapton-epoxy, the free epoxy functions of the medium are saturated with a 1×super-blocking buffer or SBB solution, in a solution comprising tris, 1 mM of sucrose and a concentration of 5% of dextran for 30 minutes at room temperature, gently stirred. The support may be washed three times with a buffered saline solution of tris, or solution of 1X TBS type, also comprising 1 mM of sucrose and 0.1% of polysorbate 20, this solution also being used for washing the antibody matrix in a process according to the present invention. The persistent fixing of antibody to the support may be analyzed by means of a fluorescent scanner, and the absence of phosphorus may be confirmed by LIBS.

In order to allow extraction of the antigen target, the lymphocytes are pelleted by centrifugation for two minutes at a speed of 10 000 revolutions/minute, placed in a microwave oven at a power of 450 W for 15 seconds, and then resuspended in a buffered solution comprising 0.1 M of tris and 1 mM of sucrose at a protein concentration of 1 mg/ml.

For the protein-antibody coupling, the proteins are diluted to a concentration of 0.1 mg/ml in a 1×SBB buffered solution comprising 1 mM of sucrose, and incubated for 12 hours at a temperature of 4° C. The antibody matrices resulting therefrom are washed in a buffered saline solution of tris (1×TBS) comprising 1 mM of sucrose, and 0.1% of polysorbate 20, and twice in a buffered saline solution of tris (1×TBS) comprising 1 mM of sucrose for 15 minutes with stirring, and then dried at room temperature.

As regards the analysis via a reference method, an aliquot of lymphocytes irradiated at each dose is analyzed by means of a fluorescence-activated cell sorter, or FACS. The cells are washed without heating in a PBS buffer before fixing and permeabilizing in ethanol of 70° proof for one hour at a temperature of 4° C. The cells are then incubated at room temperature with an anti-γH2AX$^{ser139}$ antibody solution in a PBS comprising 2% of FCS. After washing and centrifugation a pellet is obtained, which is resuspended and incubated for one hour with an anti-mouse secondary antibody labeled with a fluorophore of fluorescein isothiocyanate type, or FITC. The cells are then washed, centrifuged and resuspended in a PBS comprising propidium iodide and ribonuclease. At least $10^4$ cells were analyzed using a flow cytometer and the fluorescence intensity of each cell was determined by means of suitable analytical software. The amount of γH2AX in a given irradiated sample could then be determined from the median fluorescence intensity of the analyzed cells.

Analysis of Biochips for Phosphorus Quantification Via LIBS

The Kapton-epoxy supports on which the proteins are fixed may then be analyzed via LIBS, for example by means of a laser microprobe, with means for XY movement configured to move the support with speed and precision. The wavelength of the ablation laser beam used is chosen to be close to the wavelengths of the compound forming the adduct: for the example described, a neodymium-doped yttrium-aluminum garnet pulsed laser, or Nd:YAG laser, with a wavelength of 266 nm and an energy of 4 mJ per 5 ns pulse, is used. Two reflective mirrors can guide the laser beam to sweep the surface of the support. At the start of its optical path, the laser beam can pass through a diaphragm and then be focused on the surface of the sample to be analyzed by a refractive microscope objective lens. The position of the sample may be visualized and adjusted by the movement means using images provided by a CCD camera located above the laser microprobe. Samples may be positioned and fixed via fixing means, for example formed by screws, onto the XY movement means. The movement means can operate at a frequency of 10 hertz, corresponding to the laser firing frequency in an external synchronization mode, with movements of 30 μm between two consecutive laser firings.

For the plasma analysis, an optical fiber may, for example, be placed with one end as close as possible to the plasma, the optical fiber guiding the light arising from the plasma to an inlet slit of a spectrometer equipped with a pulsed intensified CCD camera (or ICCD camera). For example, the spectral resolution may be equal to 0.032 at 410 nm, for an inlet slit of 100 μm. The movement means and the ICCD camera may be controlled, for example, via suitable control means, for example formed by a single microcomputer.

The pulsed laser and the ICCD camera may be controlled via control means controlling the entire analytical device.

A laser firing may be applied, and a spectral window, for example extending into the wavelength range from 248 nm to 258 nm, around the spectral line intrinsic to phosphorus (253.563 nm) may be acquired, and digitized and then stored in the memory via suitable means. The control means can then impose on the movement means a movement of the sample to a new position.

Advantageously, a tube may be fixed to a fixed part of the laser microprobe and make it possible to form means for generating a stream of gas, such as argon, close to the surface of the sample on which the plasma is generated. In this way, the magnitude of the plasma emission may be increased, and the auto-absorption phenomena reduced.

The chosen intensities of the phosphorus lines at 253.563 nm (IP253) are processed as sharp values by subtracting the spectral background intensity corresponding to the mean value of the intensities measured at 254.120 nm and 254.700 nm. The target proteins may be quantified by summing all the sharp values of the IP253 lines.

The phosphorus and boron spectra may be filtered with a reliability factor Cdb determined by means of the following relationship:

$$C_{db}=[((I_B-N_B)-\sigma_N)/((I_B-N_B)+\sigma_N)] \quad (1),$$

in which $I_B$ denotes the intensity of boron, $N_B$ and $\sigma_N$ denote, respectively, the mean value and the standard deviation of the base intensity around the wavelengths 249.084 nm and 250.363 nm, calculated on all the spectra.

The phosphorus values for the target protein may then be quantified from the selected spectra using the following relationship:

$$\text{Value}P=\Sigma[(IP_{253}-nP_{253})/(IB_{249}-nB_{249})] \quad (2),$$

in which $IB_{249}$ and $IP_{253}$ denote the intensity values of the spectral lines for boron and phosphorus, respectively, and nP253 and nB249 denote, respectively, the mean intensity of the background around boron and phosphorus in a given spectrum, and corresponding to a sweep pixel of the medium surface by LIBS.

The invention claimed is:

1. A process for the quantitative analysis by optical emission spectroscopy of a plasma induced by a laser beam of at least one target included in a biochip, comprising using an adjuvant allowing the formation of a dry matrix capable of being ablated simultaneously with the at least one target, the dry matrix being configured to improve the analytical properties of plasma, the adjuvant having an emission spectrum whose lines have wavelengths distinct from the wavelengths of the spectral lines used for the quantitative analysis of said at least one target.

2. The process as claimed in claim 1, wherein the at least one target is segregated on the biochip by at least one probe such that a probe-target complex is formed between each probe and the target corresponding thereto.

3. The analytical process as claimed claim 1, wherein the use of an adjuvant (202) allows the formation of a dry matrix of amorphous structure.

4. The analytical process as claimed in claim 1, wherein the use of an adjuvant allows the formation of a dry matrix of crystalline structure.

5. The analytical process as claimed in claim 2, wherein the dry matrix is formed such that the probe-target complexes are located at the surface of a support, and are totally or partially englobed by a volume of the dry matrix.

6. The analytical process as claimed in claim 2, wherein the dry matrix and the probes are fixed to a support.

7. The analytical process as claimed in claim 2, wherein the adjuvant molecules forming the dry matrix are directly complexed to the probes.

8. The analytical process as claimed in claim 2, wherein the adjuvant molecules forming the dry matrix are fixed to a support, the probes being fixed to the adjuvant molecules, the adjuvant molecules being fixed to the support.

9. The analytical process as claimed in claim 2, wherein a layer of dry matrix is formed by placing a layer of adjuvant on the surface of the support, prior to placing the probes on the surface of dry matrix thus formed at the surface of a support.

10. The analytical process as claimed in claim 1, wherein the dry matrix is formed by a compound whose absorption wavelengths are close to the wavelength of the laser beam, such that the wavelength used for the laser is included in the absorption spectrum of the dry matrix.

11. The analytical process as claimed in claim 1, wherein the adjuvant comprises a solution of water and of an element from the group comprising sugar, polysaccharide and disaccharide.

12. The analytical process as claimed in claim 1, wherein each probe is labeled with a normalization element forming an internal standard.

13. The analytical process as claimed in claim 11, wherein each probe is labeled with the normalization element by grafting.

14. The analytical process as claimed in claim 11, wherein the normalization element is formed from boron.

* * * * *